United States Patent [19]

Daly et al.

[11] Patent Number: 4,638,801

[45] Date of Patent: Jan. 27, 1987

[54] LASER OPHTHALMIC SURGICAL SYSTEM

[75] Inventors: Richard T. Daly, Huntington; Stephen L. Trokel, New York, both of N.Y.

[73] Assignee: Lasers for Medicine, Hauppauge, N.Y.

[21] Appl. No.: 790,637

[22] Filed: Oct. 23, 1985

Related U.S. Application Data

[63] Continuation of Ser. No. 511,191, Jul. 6, 1983, abandoned.

[51] Int. Cl.[4] ............................................. A61B 17/36
[52] U.S. Cl. ................................................. 128/303.1
[58] Field of Search .................... 128/303.1, 395–398; 219/121 LM, 121 LS, 121 LT, 121 LZ

[56] References Cited

U.S. PATENT DOCUMENTS

| | | | |
|---|---|---|---|
| 3,703,176 | 11/1972 | Vassiliads et al. | 128/303.1 |
| 3,710,798 | 1/1973 | Bredemeier | 128/395 |
| 3,769,963 | 11/1973 | Goldman et al. | 128/303.1 |
| 3,783,874 | 1/1974 | Koeski et al. | 128/303.1 |
| 3,828,788 | 8/1974 | Krasnou et al. | 128/303.1 |
| 4,164,222 | 8/1979 | Prokhorov et al. | 128/303.1 |
| 4,289,378 | 9/1981 | Remy et al. | 128/303.1 |
| 4,309,998 | 1/1982 | Aron nee Rose et al. | 128/303.1 |
| 4,338,508 | 7/1982 | Jones et al. | 219/121 LS |
| 4,409,979 | 10/1983 | Roussel et al. | 128/303.1 |
| 4,417,123 | 11/1983 | Keller et al. | 219/121 LS |
| 4,499,897 | 2/1985 | Roussel | 219/121 LS |

FOREIGN PATENT DOCUMENTS 2611933  9/1977  Fed. Rep. of Germany ... 128/303.1

*Primary Examiner*—Edward M. Coven
*Assistant Examiner*—Max F. Hindenburg
*Attorney, Agent, or Firm*—Kane, Dalsimer, Kane, Sullivan and Kurucz

[57] ABSTRACT

An ophthalmic slit lamp is modified by adding a laser to it to be used for microsurgery. The laser is mounted on the lamp so its beam is projected into the eye along one axis while the normal viewing image generated by the lamp is focused into the eye from another angle. An aiming image is focused into the eye coincidentally with the laser beam so that the distance between the two images and their relative position may be determined by their apparent positions as seen from the viewing binoculars of the lamp.

10 Claims, 5 Drawing Figures

LASER OPHTHALMIC SURGICAL SYSTEM

This is a continuation of co-pending application Ser. No. 511,191, filed July 6, 1983, now abandoned.

FIELD OF INVENTION

The present invention pertains to eye surgery by use of lasers and more particularly to a method and apparatus for focusing and aiming a laser beam accurately within a patient's eye.

DESCRIPTION OF THE PRIOR ART

Performing eye surgery by focusing a non-visible, high-power pulsed laser beam on nominally transparent tissues of a patient's eye has been shown to be efficacious. Such operations have been successfully performed to overcome various defects in the eye; for example, following catarectomy, where the natural lens has been replaced with an intraocular lens. Frequently within 2 to 4 years thereafter, the posterior tissue of the lens capsule becomes opaque and must be opened. Non-invasive laser surgery of this type has been used successfully for this operation.

Typically a laser ophthalmic microsurgical system is made by modifying an ophthalmic slit lamp apparatus to permit the precise aiming and focusing of the laser beam onto nearly transparent tissues within the eye (the "Target Tissues"). An ophthalmic slit lamp apparatus is a device long used to make careful diagnostic observations inside the eye. One such instrument is made by TOPCON corporation and is described in their publication No. 8202-30SK. The ophthalmic slit lamp apparatus comprises a binocular viewing microscope and a light source assembly (the "Slit Lamp"). The slit lamp projects a generally elongated or slit-shaped illuminated image into the eye which is then observed through the binocular viewing microscope. The binocular microscope is mounted on a first arm while the slit lamp is mounted on a second arm. The two arms are independently rotatable around a common vertical axis which contains their common focus. The illuminated slit image is focused on a particular "transparent" tissue (the "Target Tissue") such as the cornea, front lens surface, rear lens surface or transparent bands lying generally in planes normal to the slit image rays. As the rays from the slit lamp pass through the tissue, even a small amount of light scatter by the tissue renders the slit image visible when observed through the binocular microscope. By rotating the slit lamp and/or the binocular arms differentially, the physician is able to view the chosen tissue in various aspects by the scattered light. The slit-image together with the microscope field of view is moved within the eye by a manual joystick control on the apparatus either laterally (for lateral aiming) or toward or away (for focusing). A second control knob is used for vertical adjustment.

In the current art, the above-described device has been modified for performing microsurgery by directing and focusing a high power, pulsed laser beam into the eye by means of an additional set of optics "piggybacked" on the slit lamp apparatus. To locate or identify the exact path and focal position of the laser beam, a low intensity visible aiming beam coincident with the laser beam is arranged to focus at a point in space coincident with the slit-image and the laser beam focal spot. This is accomplished by mounting, on the ophthalmic slit lamp apparatus, a dichroic mirror which reflects the aiming beam and the coincident laser beam into the eye along an optical axis lying in the same plane as that of the binocular microscope and the slit image rays. Typically a low intensity helium-neon laser is used for the aiming beam.

This scheme leads to two major difficulties. First, the physician is often forced to observe the eye tissue during operation through the added dichroic mirror. Such mirrors inherently cause astigmatism, degrading the physician's view. Secondly, the initial focus position of the aiming beam and slit image, in general, does not lie exactly in the plane of the Target Tissue. Thus the physician first sees an unfocused aiming beam scattered from the Target Tissue and must "hunt" for the focus by shifting the slit-image with his joystick until scattering of the aiming beam appears sharpest and of minimum size. Because the aiming image size changes only slowly near the correct focus position, this technique makes it difficult to quickly adjust to the correct focal position since it presents the same "out-of-focus" aspect independent of whether the target tissue is in front of or behind the aiming image focal position.

In other schemes, two mutually converging aiming beams disposed symmetrically about the laser beam axis are used which define the laser beam focus at their intersection point. Here, in general, two blurry images are initially seen by scattering from the tissue which only coalesce and become sharp when their convergence lies in the plane of the tissue. However, in either case the focus point must be found by "hunting" since even with two aim beam images, no indication as to the position-in-depth of the focus is conveyed.

OBJECTIVES AND SUMMARY OF THE INVENTION

In view of the above, an objective of the present invention is to provide a system in which the aiming beam and the slit-image cooperate to permit rapid determination of whether their common focus lies in front of, behind or exactly on the Target Tissue. Another objective is to provide a system in which the dichroic mirror and its undesirable effects are eliminated. Further objectives and advantages shall become apparent in the description below.

According to this invention a laser ophthalmic microsurgical system comprises a slit lamp which focuses the image of an illuminated vertical slit along a first axis, a binocular microscope which provides for viewing along a second axis and a laser/aiming system which projects a laser beam and aiming beam along a third axis. The said first and second axes lie in a common horizontal plane which does not include said third axis. All three axes converge to a common point (the "Common Focus") with the said third axis preferably approaching the Common Focus from below the horizontal plane defined by said first and second axes.

A further modification of the slit lamp according to the present invention is the provision of a fiducial feature about midway along the long dimension of the vertical slit image—a short unilluminated section, for example. This feature is located at and defines the "common focus". Note that, due to the approach to the common focus along non-coincident axes by the slit image and aiming beam rays, if these rays are intercepted by a scattering tissue lying, say, slightly in front of the common focus, the observed scattering will give rise to slightly out-of-focus images of the aiming beam and slit fiducial feature which are not coincident, but are displaced vertically from each other. In the case cited, the aiming beam scattering will appear below the fiducial feature scattering. When the scattering tissue lies behind the common focus, the aiming beam will appear above the fiducial feature. With these clues, the physician can determine in which direction and approximately how far to move the slit lamp apparatus to bring the common focus exactly onto the scattering tissue which is indicated by seeing the aiming beam and fiducial feature scattering from the same point.

DESCRIPTION OF THE PREFERRED EMBODIMENT

Figure 1:
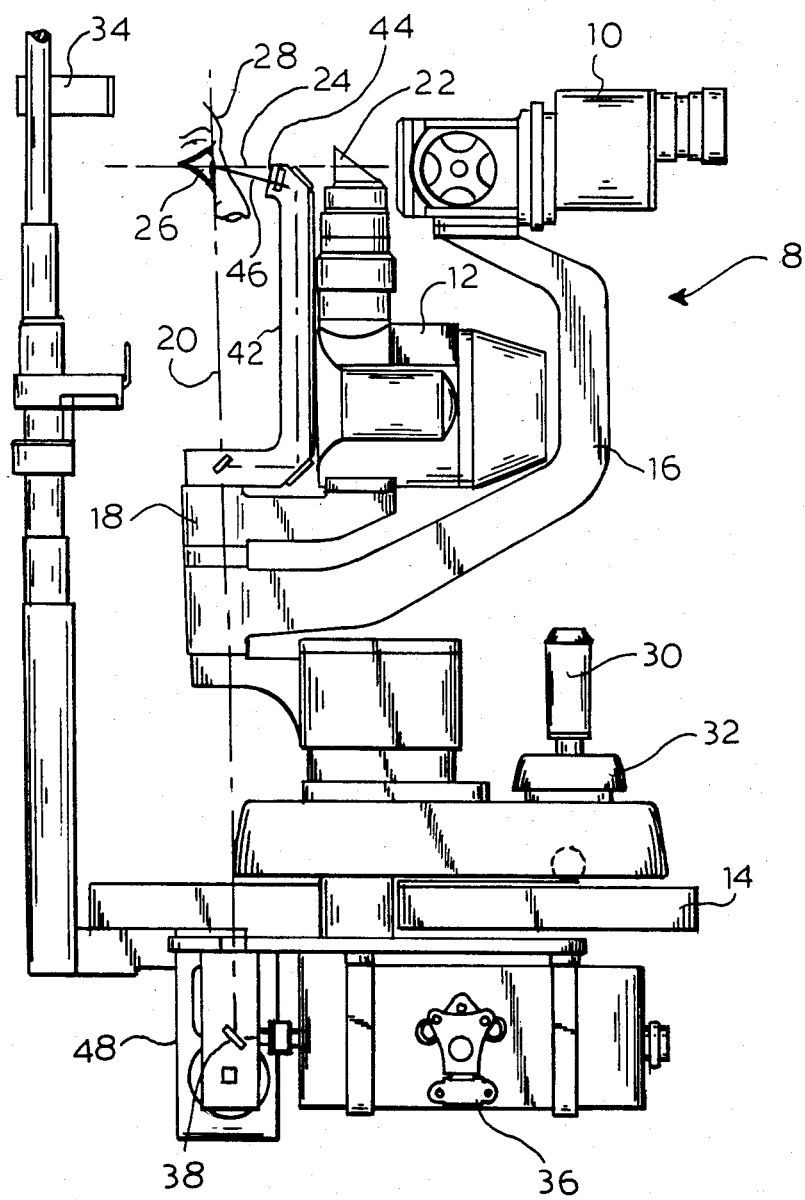
FIG. 1 shows a side view of a slit lamp in which the present invention has been incorporated.

An ophthalmic slit lamp apparatus 8 modified in accordance with the present invention is shown in FIG. 1. As described above, it comprises a binocular microscope 10 and a light source 12 mounted on a common base 14 by arms 16 and 18 respectively. The arms are mounted so that the microscope binoculars and the light source may be rotated independently around a common vertical axis 20. Light source 12 generates an illuminated slit image which is projected by prism 22 along a first optical axis 24 into the eye 26 of patient 28. The vertical slit image focused into the eye may be observed by a physician through the binoculars either along the first optical axis 24 or along a different, second axis which lies in the same horizontal plane with said first optical axis. The binocular microscope and slit lamp assembly are simultaneously shifted in two directions by joystick 30, namely laterally and toward or away from the patient 28. The binocular microscope and slit lamp assembly may be simultaneously shifted vertically by turning collar 32. A bracket assembly 34 is provided to keep the head of patient 28 steady while the subject device is in use.

Figure 4:
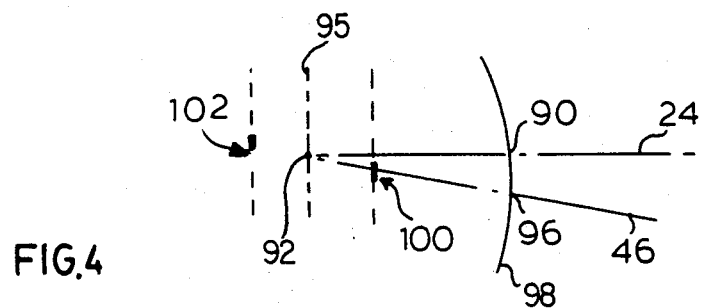
FIG. 4 is a side-sectional view of the eye showing the optical axes and the slit and aiming images.

A laser 36 is attached to the base of the slit lamp apparatus 8 so that its laser beam is reflected upward by mirror 38 along the vertical axis 20 and enters a laser beam guide 42 and is focused into the eye by the objective lens 44 along a third optical axis 46. The two optical axes 24 and 46 may or may not lie in the same vertical plane but they always intersect in the eye 26, as shown in FIG. 4 at an angle of 5° to 15°.

Figure 2:
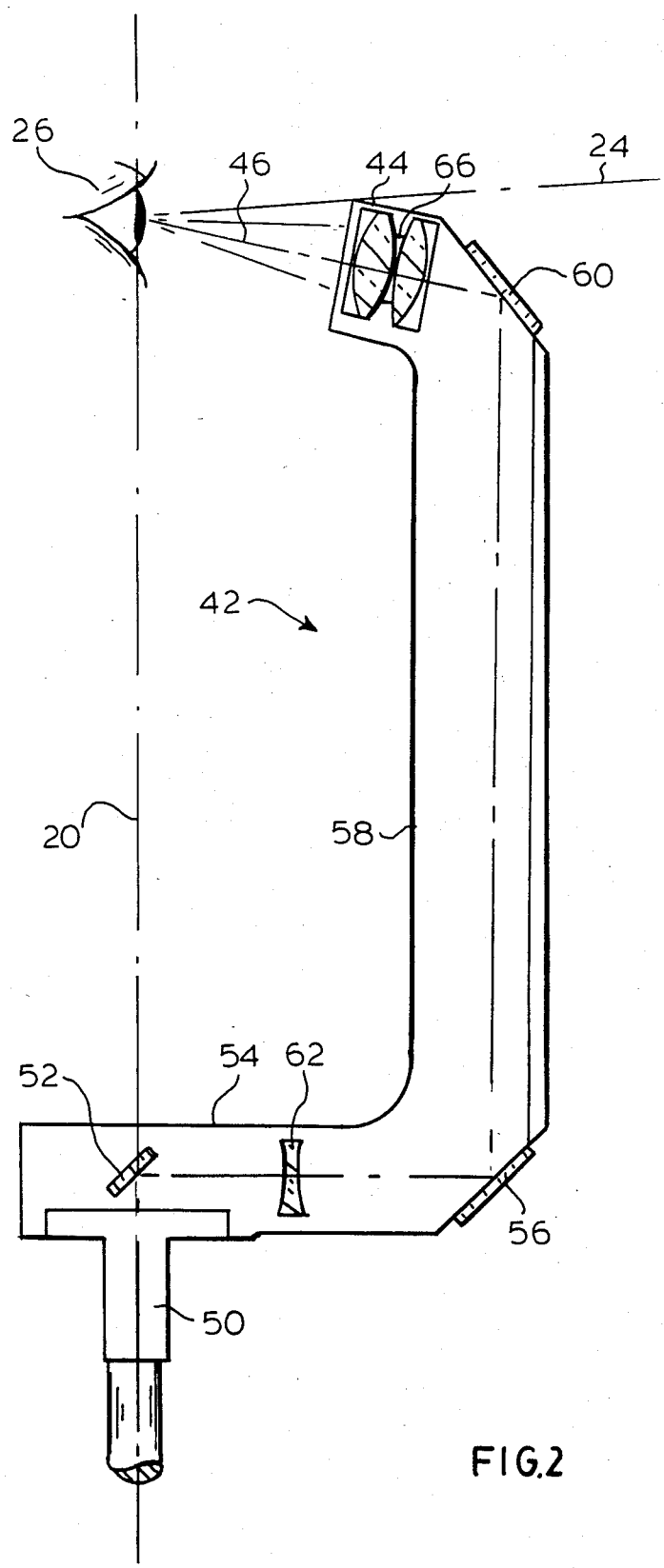
FIG. 2 shows details of the laser beam guide.

As can be seen in FIG. 2, the laser beam guide 42 is generally L-shaped. The beam from the laser 36 enters through a bottom port 50 along axis 20 and is propagated to the output port 44. The optical path through the guide is controlled by a first mirror 52 which directs the beams along the short horizontal leg 54 of the guide, and a second mirror 56 which directs the beams along the long, vertical leg 58. Finally a third mirror 60 reflects the beam out through the objective lens 44 at the desired angle. The guide is also provided with lenses 62 and 66 to process the beam.

Figure 3:
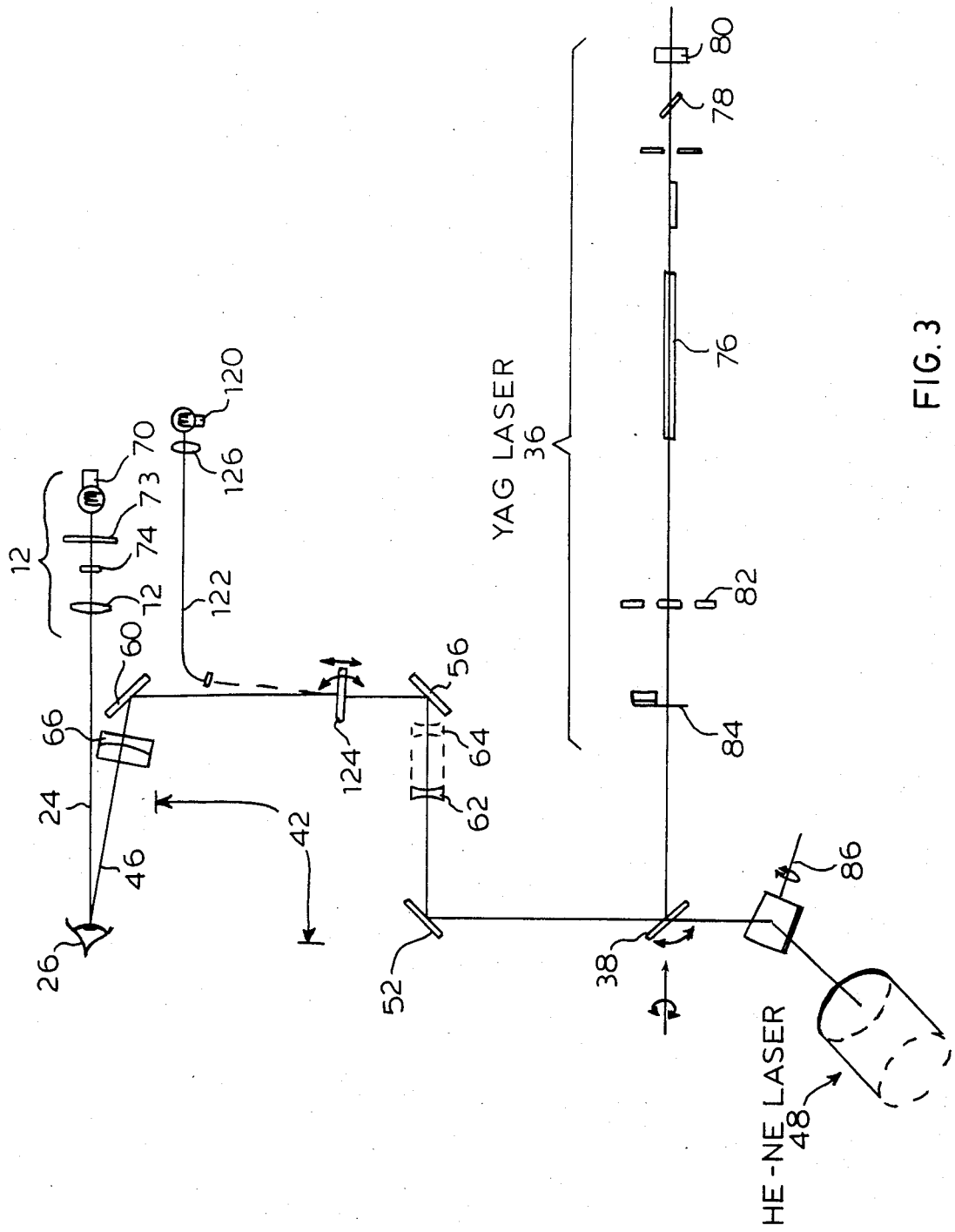
FIG. 3 is a schematic diagram of the invention.

An aiming means is also shown in FIG. 3. This aiming system comprises a light source 120, a light guide 122 and an adjustable dichroic mirror 124, placed in the path of the laser beam originating from YAG laser 36. In this embodiment the light from source 120 is shaped into an aiming image by lens 126 and sent along guide 122 to the mirror 124. The mirror then sends both the laser beam and the aiming image coincidently towards the eye. The guide 122 preferably comprises a bundle of optical fibers. The aiming image generated from source 120 may have any desired shape such as a dot, a bar, and X, etc., although a bar-shape is preferable.

An alternative aiming means is also shown in FIG. 3. It consists of a low powered continuous visible helium-neon laser, 48, attached to the base of the slit lamp 8 and directed by a mirror 86 so that it can project an aiming image along the same optical path as the path of the laser beam emitted by the first laser.

The optical elements of the subject device are shown in a diagramatic fashion in FIG. 3. Light source 12 comprises a bulb 70 which illuminates a vertical slit 73, the image of which is focused by lens 72 into the eye 26 along optical axis 24. It is to be understood that a number of optical elements such as mirrors and lenses, which are incorporated in light source 12 have been omitted from FIG. 3 since they are not essential to the present description. A short, central portion of the slit is blocked by an aligning bar 74. The purpose and function of this bar is explained in more detail below.

Laser 36 produces the beam which is used to treat the eye tissues. It is preferably a Q-switched or mode locked YAG laser having a lasing rod 76, a Q-switching or mode-locking saturable absorber 78, a mirror 80 and attenuator elements 82. Such lasers are well-known in the art and need not be described in more detail. The output of the laser may be blocked by a laser beam shutter 84. The laser beam output comprises high-power laser pulses of several nanosecond duration at a wavelength of approximately 1064 nm.

The alternative aiming source 48 is preferably a He-Ne laser which emits a visible red laser continuous beam. A translatable and rotatable mirror 86 is used to align the red laser beam to the axis 20. Mirror 38 is an adjustable dichroic mirror and it combines the two laser outputs along axis 20 to guide 42. The elements of guide 42 have been already described.

Figure 5:
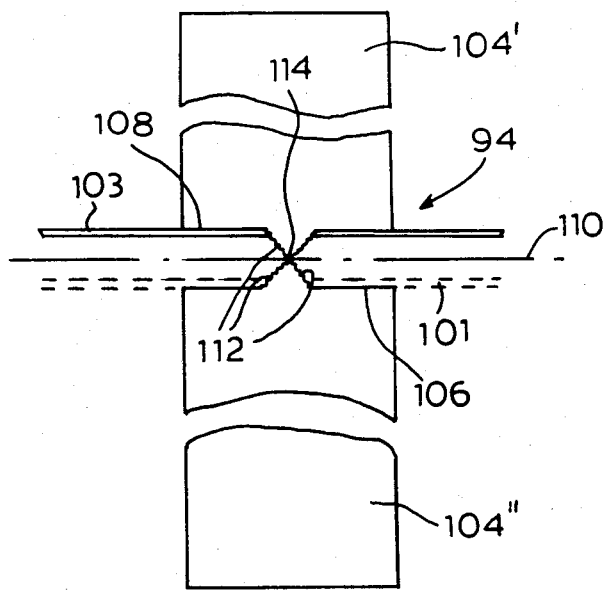
FIG. 5 is a front view of the slit and aiming images.

The paths taken by the various optical beams within the eye are illustrated in FIG. 4. For the sake of clarity, various tissues of the eye have beem omitted. The rays of the vertical slit image enter the eye at a point 90 along axis 24, surface 98 being the surface of the cornea. The laser beam and coincident aiming beam enter the eye at point 96 along axis 46. Axes 24 and 46 intersect at the common focus 92. For example, the aiming beam image is a narrow illuminated horizontal bar substantially longer than the narrow dimension of the slit image as shown schematically in FIG. 5. Initially, the common focus is either in front of the Target Tissue 95, as at 100 or behind as at 102. The respective positions of the target tissue and common focus may now be determined by the apparent position of the scattering from the aiming beam with respect to scattering from the fiducial reference of the slit image as seen through the microscope binoculars. In order to make this determination, the slit image 94 is split by aligning bar 74 (the fiducial reference). As can be seen best in FIG. 5, the slit image 104 is partitioned by dark areas 106 and 108 generated by aligning bar 74 into two segments 104' and 104". An observer looking through the binoculars would see the image 94 as shown in FIG. 5 with the two bright segments 104' and 104" separated by dark area 106 and 108 terminated by two arrows which point to the common focus point 92 also shown in FIG. 4. The illuminated horizontal bar aiming image is then either at position 102 above center line 110, (FIG. 5) corresponding to Target Tissue behind the focus or below it at position 100 corresponding to Target Tissue in front of the focus, thus giving clear indication of the relative position of the common focus with respect to the scattering target tissue. The arrows terminating dark areas 106 and 108 may be provided with step-wise gradations as at 112.

To further aid in seeing the scattering from the aiming beam rays, and to facilitate the determination of aiming beam and slit image fiducial reference relative position, the aiming beam light source may be caused to "blink" at a low rate, say 3 to 5 hz.

It is clear that numerous other modifications and alterations may be made to the subject device without departing from the scope of the invention as defined in the appended claims.

What is claimed is:

1. An apparatus for performing microsurgery on a tissue of an eye comprising:

a frame;

first and second arms rotatably mounted on said frame;

means mounted on said first arm for projecting a slit image along a first optical axis on said tissue for illuminating said tissue, said slit image comprising a first and a second segment separated by a dark area with a horizontal center line, said dark area being provided as a fiducial reference within the eye;

means mounted on said second arm for observing said slit image within the eye along a second optical axis, said first and second axis defining a horizontal plane;

a source for a laser beam having a focal point; and focusing means mounted on said first arm for focusing said laser beam into the eye by shifting said focal point along a third axis with respect to said slit image, said third axis being at an acute angle with respect to said horizontal plane;

whereby the actual position of said focal point with respect to said slit image is indicated by the relative position of said focused laser image with respect to said fiducial reference as observed along said second optical axis.

2. The apparatus of claim 1 wherein said dark area is bordered by step-wise gradations for providing a quantitative indication of said relative position.

3. The apparatus of claim 1 wherein said first and third optical axis intersect within the eye at an angle of 5° to 15°.

4. The apparatus of claim 1 wherein said laser source comprises a Q-switched or mode-locked laser.

5. The apparatus of claim 4 wherein said laser source is affixed to said frame.

6. The apparatus of claim 1 further comprising aiming means for projecting an aiming image into the eye coincident with said focal point.

7. The apparatus of claim 6 wherein said aiming means comprises a second laser source mounted on said frame.

8. The apparatus of claim 7 wherein said second laser source comprises a helium-neon laser.

9. The apparatus of claim 6 wherein said aiming means comprises a visible light source.

10. The apparatus of claim 6 wherein said laser beam and aiming image enter the eye at a point below said horizontal plane whereby the aiming image appears above said center line if it is focused behind the slit image and below the center line of said aiming image is focused ahead of the slit image.

* * * * *